(12) United States Patent
Iddan

(10) Patent No.: US 7,251,383 B2
(45) Date of Patent: Jul. 31, 2007

(54) METHOD AND DEVICE OF IMAGING WITH AN IMAGER HAVING A FIBER PLATE COVER

(75) Inventor: Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 492 days.

(21) Appl. No.: 10/722,410

(22) Filed: Nov. 28, 2003

(65) Prior Publication Data

US 2004/0115877 A1 Jun. 17, 2004

Related U.S. Application Data

(60) Provisional application No. 60/429,378, filed on Nov. 27, 2002.

(51) Int. Cl.
*G02B 6/00* (2006.01)
*A61B 1/06* (2006.01)
*A61B 1/07* (2006.01)

(52) U.S. Cl. .................. 385/12; 385/120; 600/160
(58) Field of Classification Search ................ 385/120
See application file for complete search history.

(56) References Cited

U.S. PATENT DOCUMENTS

| 4,278,077 A | | 7/1981 | Mizumoto | |
|---|---|---|---|---|
| 5,321,251 A | * | 6/1994 | Jackson et al. | 250/208.1 |
| 5,446,290 A | * | 8/1995 | Fujieda et al. | 250/556 |
| 5,604,531 A | * | 2/1997 | Iddan et al. | 348/76 |
| 5,760,852 A | * | 6/1998 | Wu et al. | 349/14 |
| 5,835,142 A | * | 11/1998 | Nakamura et al. | 348/335 |
| 5,837,196 A | | 11/1998 | Pinkel et al. | |
| 5,986,746 A | * | 11/1999 | Metz et al. | 356/71 |
| 6,240,312 B1 | | 5/2001 | Alfano et al. | |
| 6,395,562 B1 | | 5/2002 | Hammock et al. | |
| 6,885,439 B2 | * | 4/2005 | Fujieda | 356/71 |
| 2002/0001695 A1 | | 1/2002 | Tajima et al. | |
| 2002/0015952 A1 | | 2/2002 | Anderson et al. | |
| 2003/0118219 A1 | * | 6/2003 | Higuchi et al. | 382/125 |
| 2003/0133113 A1 | * | 7/2003 | Hajduk et al. | 356/367 |

(Continued)

FOREIGN PATENT DOCUMENTS

JP          06129908 A    *    5/1994

(Continued)

OTHER PUBLICATIONS

"Microarrays: their origins and applications", Roger Ekins and Frederick W. Chu, TibTech, Jun. 1999 (vol. 17), pp. 217-218.

(Continued)

*Primary Examiner*—Michelle Connelly-Cushwa
(74) *Attorney, Agent, or Firm*—Pearl Cohen Zedek Latzer LLP

(57) ABSTRACT

There is provided an imager with, for example, a fiber plate cover capable of transferring to a sensor element an image of a sample that may be close to or in contact with such fiber plate cover, and imaging such sample. An imager may include a fiber plate cover capable of capturing images from a microarray analysis device. There is also provided a method of capturing images with an imager of a sample that is for example in contact with a fiber plate cover on such imager.

9 Claims, 7 Drawing Sheets

U.S. PATENT DOCUMENTS

| | | | |
|---|---|---|---|
| 2003/0169847 A1* | 9/2003 | Karellas et al. | 378/98.3 |
| 2004/0023249 A1* | 2/2004 | Balch | 435/6 |
| 2004/0129891 A1* | 7/2004 | Takagi et al. | 250/397 |
| 2004/0218085 A1* | 11/2004 | Sugawara et al. | 348/340 |

FOREIGN PATENT DOCUMENTS

| | | |
|---|---|---|
| WO | WO 01/65995 | 9/2001 |
| WO | WO 02/055984 | 7/2002 |
| WO | WO 02/086329 | 10/2002 |

OTHER PUBLICATIONS

"The Promise of Protein Microarrays", Sinskey et al., PharmaGenomics, Jul./Aug. 2002, pp. 20, 22, 24.

Edmunds Industrial Optics' Online Catalog, Fiber Optic Tapers and Faceplates, Stock No. N55 142.

* cited by examiner

800 — CAPTURING WITH AN IMAGER AN IMAGE OF A SAMPLE IN CONTACT WITH A FIBER PLATE COVER ON SUCH IMAGER

FIG.8

METHOD AND DEVICE OF IMAGING WITH AN IMAGER HAVING A FIBER PLATE COVER

CROSS REFERENCE TO RELATED APPLICATIONS

The present application claims benefit from prior provisional patent application Ser. No. 60/429,378 filed on Nov. 27, 2002 entitled "IMAGER", and incorporated herein by reference in its entirety.

FIELD OF THE INVENTION

The present invention relates to imagers generally, and particularly to devices, systems and methods of imaging items in contact with or in close proximity to an imager.

BACKGROUND OF THE INVENTION

Imagers may be used in many applications to view an image of a scene. Some imagers may include complimentary metal oxide semiconductors (CMOS), charge coupled devices (CCD) or other imaging or sensing mechanisms. An imager may include an optical system that may incorporate, for example, lenses, mirrors and/or prisms. The optical system may alone or in combination with other devices focus an image on for example an image sensing device or image sensing elements of an imaging sensing device. An optical system may magnify or reduce the image of the subject being imaged and may perform other optical corrections. Reference is made to FIG. 1, which depicts an optical system 10 providing an image of a scene 12 to an imager 14. Imager 14 may include for example a detector 17 having one or more sensing or sensor elements 18 and a glass cover 19. Sensing or sensor elements 18 may correspond, for example, to individual pixels or sensing elements of an imager such as a CCD or CMOS imager. Optical system 10 and imager 14 may be housed in for example a housing 16, which may keep components of the imager 14 in fixed location relative to other components of the imager and relative to the optical system. A fixed or minimum distance may be maintained between optical system 10 and imager 14, and a minimum distance may be required in the prior art between optical system 10 and a sample or object to be imaged. Other suitable constructions and configurations for imaging systems may be used.

SUMMARY OF THE INVENTION

A device according to an embodiment of the invention includes an imager with a set of sensor elements, and a fiber plate cover disposed on the set of sensor elements.

An autonomous in vivo device according to an embodiment of the invention includes an imager and a fiber plate cover disposed on such imager, where the fiber plate cover transfers to the imager an image of an object in contact with the fiber plate cover.

A microarray analysis device according to an embodiment of the invention includes an imager, a fiberplate cover disposed on such imager, and an interaction chamber for containing a sample, where the fiber plate cover is configured to transfer an image of the sample to the imager.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may understood by reference to the following detailed description when read with the accompanying drawings in which:

FIG. 8 is a schematic flow chart diagram presentation of a method in accordance with certain embodiments of the present invention.

Figure 1:
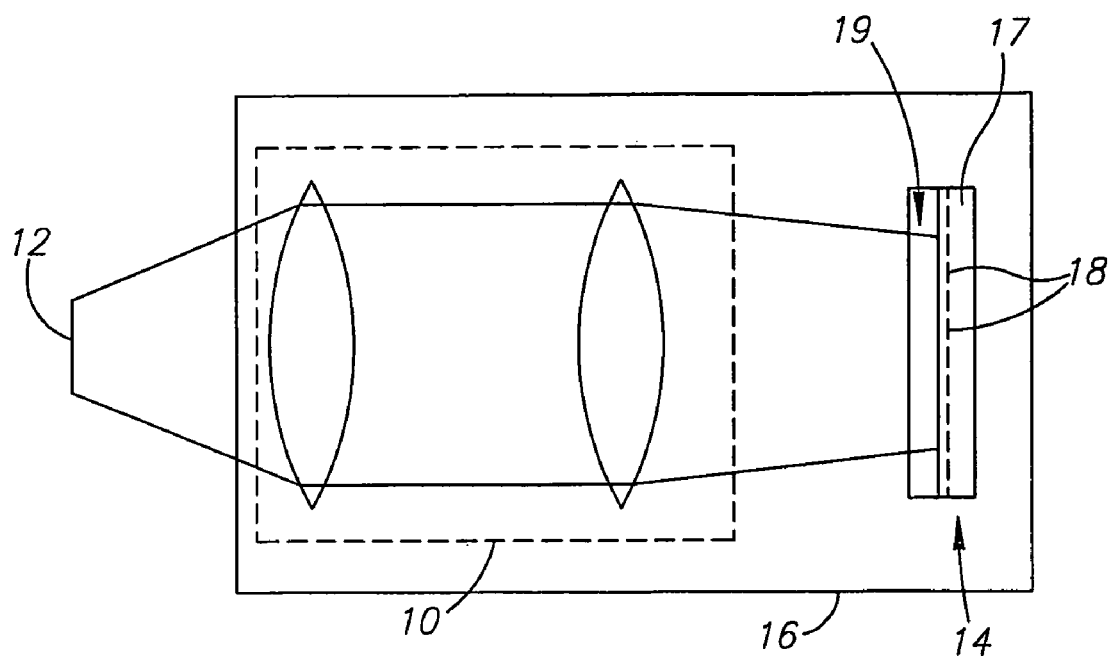
FIG. 1 is a schematic illustration of a prior art imager and optical system.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 2A:
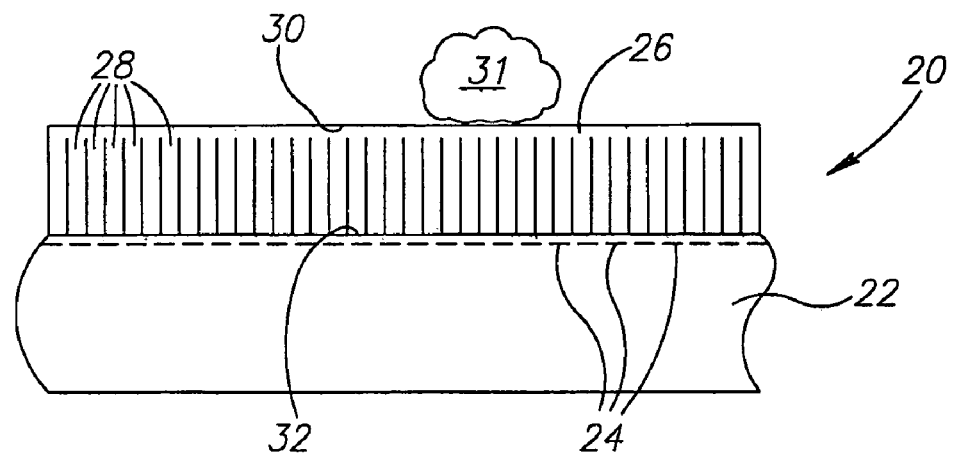
FIG. 2A is a schematic illustration of an imager, constructed and operative in accordance with an embodiment of the present invention.

Reference is made to FIG. 2A, which illustrates an imager 20, constructed and operative in accordance with an embodiment of the present invention. Imager 20 includes, for example, a detector 22 having a set (wherein set may include one unit) of sensing or sensor element(s) 24 and, in accordance with an embodiment of the present invention, a fiber plate cover 26. Sensing or sensor elements 24 may correspond, for example, to individual pixels or sensing elements of an imager such as a CCD or CMOS imager. In an embodiment of the invention, fiber plate cover 26 may be attached directly to detector 22 and may be capable of transferring, directing or conveying an image of for example a sample 31 in contact with an outer surface 30 of such fiber plate cover 26, to sensor elements 24 which are located proximate to or in contact with an inner surface 32 of fiber plate cover 26. In some embodiments, sensor elements 24 may not receive light that is reflected from sample 31 back to imager 20. Sensor elements 24 may in some embodiments capture images of sample 31 using primarily transmitted light coming towards imager 20 from the direction of such sample 31, rather than using light reflected from sample 31.

Detector 22 may include a suitable imaging device such as for example a CMOS, a CCD, a bolometer or an IR sensor array, or a combination of such devices. Detector 22 in some embodiments may be capable of detecting color. Other suitable imaging devices may be used. Fiber plate cover 26 may be formed of a fiber plate, such as for example a plate formed of a plurality of short fibers 28 such as optical fibers aligned for example in parallel. Such short optical fibers 28 may in some embodiments be configured at a generally perpendicular angle to the alignment of sensor elements 24. An exemplary fiber plate may be found in the Edmund Industrial Optics' Catalog, page 116, part number NT55 142. Other suitable fiber plates or amalgamations of fibers may be used. Fibers 28 may be made of glass, plastic or other materials suitable for carrying, transferring or conveying light, images or other electromagnetic waves. In some embodiments, for a set of fibers 28 and a set of sensor elements 24, a single fiber 28 such as for example an optical fiber, may be aligned with a single sensor element 24 so that an image or a portion of an imager transferred by a fiber 28 reaches a designated or identifiable sensor element 24, for example a pixel. In some embodiments, more than one fiber 28 may transfer an image to a single sensory element 24, or a single fiber 28 may transmit an image to more than one sensor element 24.

Fiber plate cover 26 may in some embodiments serve as a cover, barrier, or part of a container. For example, fiber plate cover 26 may replace or supplement glass cover 19 as is shown in FIG. 1, which may protect sensor element 24 from the environment. Fiber plate cover 26 may be mounted onto detector 22 with a suitable adhesive such as for example a glass adhesive, an ultraviolet light (UV) curable adhesive, or other suitable adhesive, for example in a manner similar to the mounting of the glass or other covers or domes of the prior art onto their detectors or by other mechanical or chemical reaction methods. In some embodiments, fiber plate cover 26 may be the only separation or protection between a sensor element 24 and a sample 31, such that there is direct contact between a sample 31, fiber plate cover 26 and sensor element 24. In some embodiments, direct contact may not be needed between a sample 31 and outside surface 30, such that a sample 31 may be located from, for example, 1 mm to several millimeters away from outer surface 30 of fiber plate cover 26. Other suitable dimensions may be used. In some embodiments, a transparent cover or coating may be added or applied to outer surface 30 for purposes of for example protection. For purposes of this application, notwithstanding such cover, coating or small distance between a sample 31 and outer surface 30, a sample 31 may still be considered in contact with fiber plate cover 26.

According to an embodiment, fiber plate cover 26 may operate optically, as a fiber optic element, and may coherently transfer an image of the sample 31 that reaches its outer surface 30 to sensor element 24. According to an embodiment of the invention an image reaching an outer surface 30 may not be processed optically, but may rather be shifted or transferred from outer surface 30 to inner surface 32, while generally coherently preserving the image. In such embodiments, the size of the sample 31 in the image transferred to sensor elements 24 may be the same as the size of the image of sample 31 in the image reaching outer surface 30.

In some embodiments focusing or registration of the image onto sensor elements 24 may not be required. Thus, according to embodiments of the invention, imager 20 may image a scene or sample 31 that reaches or makes contact with its outer surface 30 without the use of an optical system. In some embodiments, the size of a sample 31 in an image reaching outer surface 30 may be equal to the size of the sample 31 that reaches sensor element 24, such that no magnification or reduction in scale is performed by fiber plate cover 26.

It will be appreciated that imager 20 may be a compact, lensless imaging system. Such an imaging system may be useful, for example, in devices that may perform imaging in a restricted space such as for example in a body lumen. In some embodiments, imager 20 may be suitable for imaging items in direct contact with outer surface 30. Imager 20 may be placed against a "scene" or sample 31 to be viewed and, in the presence of light, may generate or capture an image of sample 31.

Embodiments of the invention may be included in an autonomous device such as for example self-contained in-vivo devices that are capable of passing through a body lumen such as for example a GI tract, the reproductive tract, the urinary tract or a blood vessel, and where some or all of the operative components are substantially contained within a container, and where the device does not require wires or cables to for example receive power or transmit information. For example, power may be supplied by an internal battery or wireless receiving system. Other embodiments may have other configurations and capabilities. For example, components may be distributed over multiple sites or units. Control information may be received from an external source.

Examples of in-vivo sensors that may be used with the present invention are described in U.S. Pat. No. 5,604,531 to Iddan entitled "An In-vivo Camera Video System", in International Application Publication No. WO 01/65995, entitled "A Device and System for In-Vivo Imaging", both of which are assigned to the common assignee of the present invention and are hereby incorporated herein by reference. Other suitable sensing devices may be used. In other embodiments an autonomous in-vivo device need not be used. For example, an endoscope requiring external connections may incorporate an imaging system including a fiber plate cover or fiber optic system as described herein. While a device or method in accordance with some embodiments of the invention may be used for example in a human body, the invention is not limited in this respect. For example, some embodiments of the invention may be used in conjunction with or inserted into a non-human body, such as for example a dog, cow, rat or other pets or laboratory animals.

Figure 2B:
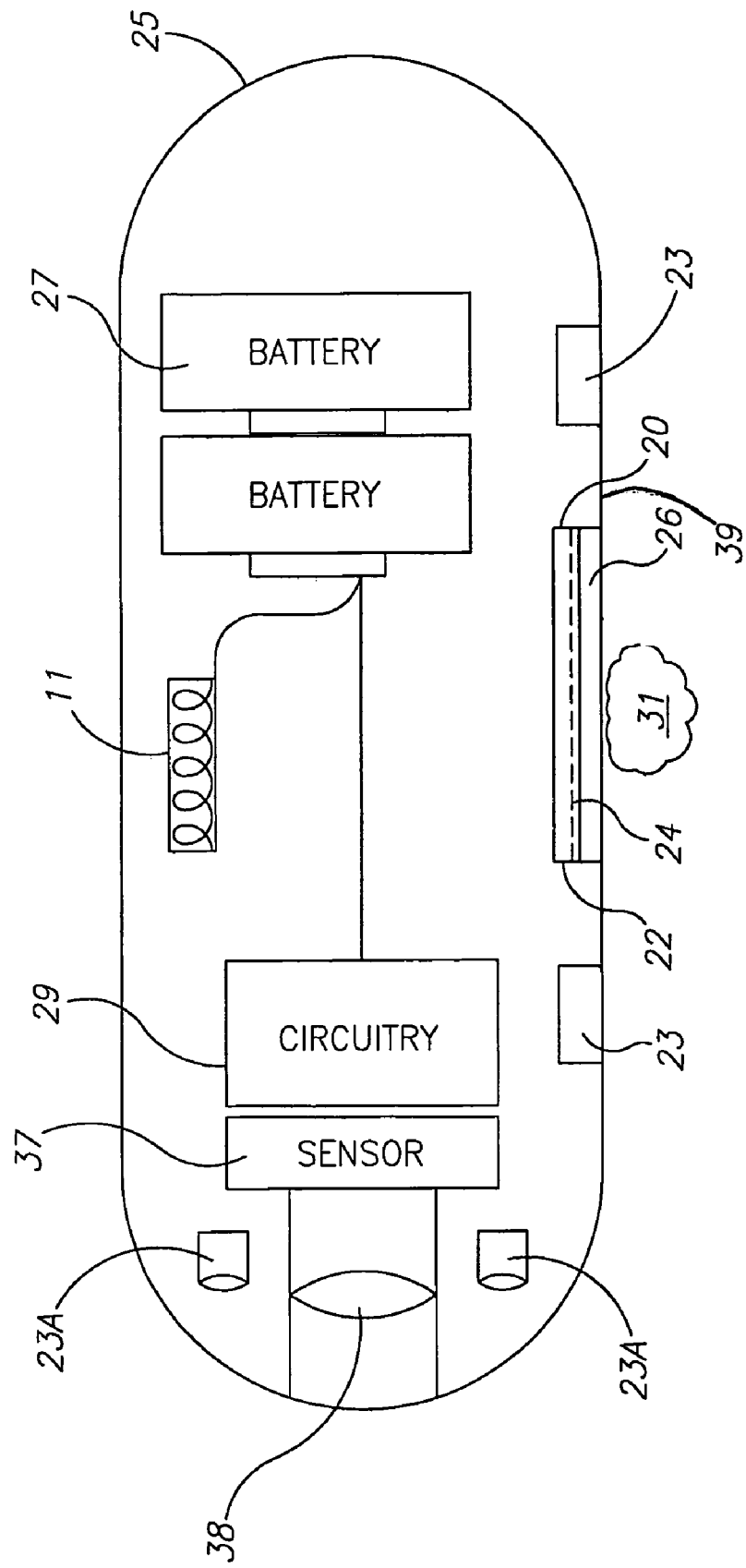
FIG. 2B is a schematic illustration of an imager included in an in-vivo device in accordance with an embodiment of the invention.

Reference is made to FIG. 2B, a schematic illustration of an imager included in an in-vivo device in accordance with an embodiment of the invention. In the case of an in-vivo device with a shape as shown, imager 20 may for example be configured on a side (e.g., a relatively flat or long side) of an in-vivo device 25 where imager 20 may come into contact with fluids, endo-luminal walls or other materials, objects or samples 31 that may be found for example in an endo-luminal cavity. In some embodiments, fiber plate cover 26 may be part of or contiguous to or part of a container, shell or an outer wall 39 that surrounds device 25. In one embodiment, fiber plate cover 26 in conjunction with container or outer wall 39 and possibly other elements (e.g., an optical dome, a sealing unit, etc.), may completely or substantially completely enclose the elements of device 25. Illuminating elements 23, such as for example light emitting diodes or other illuminating elements 23 may provide light that may be reflected back through fiber plate cover 26 to sensor elements 24. In some embodiments, imager 20 may be configured on an end or other area of device 25. In some embodiments, device 25 may include a transmitter 11, one or more batteries 27 and control circuitry 29. In some embodiments, transmitter 11 may transmit signals using for example radio frequencies to an outside receiver, not shown. Such signals may include for example image signals or signals carrying other data or instructions. In some embodiments, device 25 may include an additional imaging system such as for example a lens 38, an image sensor 37 such as for example a CCD, and illuminating elements 23A. Devices having other suitable shapes and configurations may be used.

It will be appreciated that in some embodiments, imager 20 may capture images of a sample 31 using light that is reflected back towards sensors elements from the direction of a sample 31.

Figure 3A:
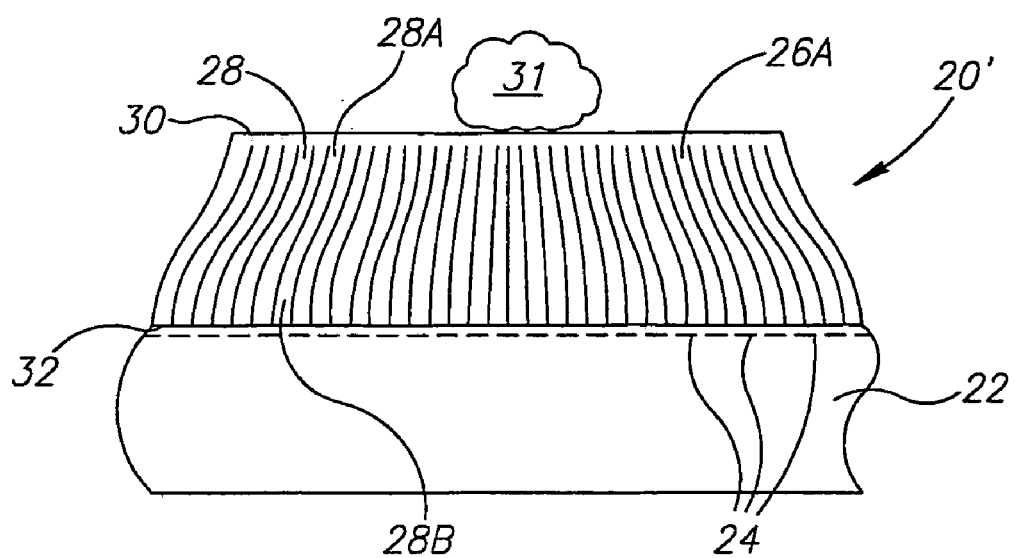
FIGS. 3A and 3B are schematic illustrations of imagers with optical capabilities, constructed and operative in accordance with an embodiment of the present invention.
Figure 3B:
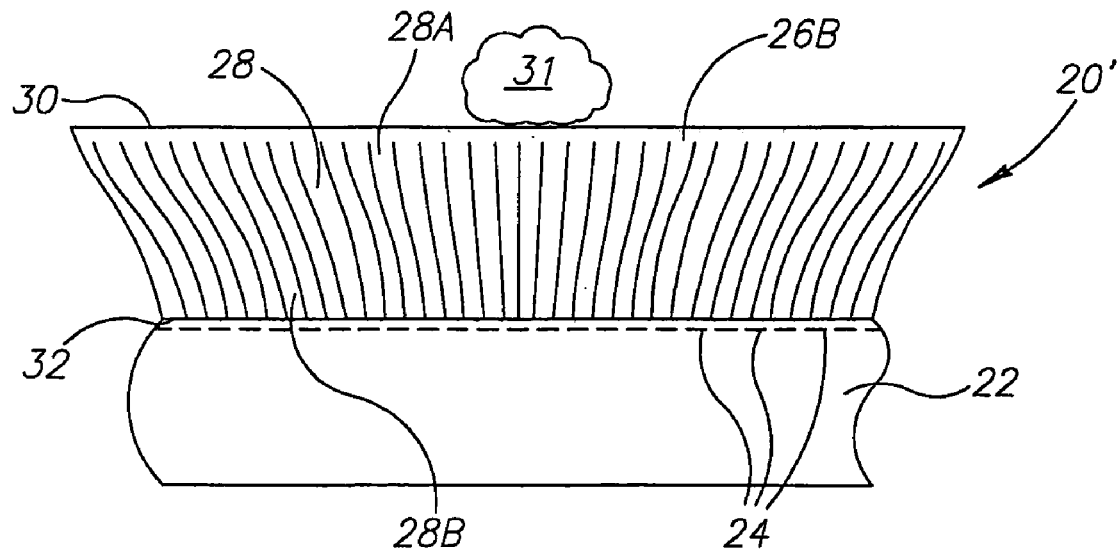

Reference is made to FIGS. 3A and 3B, schematic illustrations of imagers with optical capabilities, constructed and operative in accordance with an embodiment of the present invention. In embodiments of the invention shown in FIGS. 3A and 3B, fibers 28 of fiber plate cover 26A may be tapered or otherwise of different diameters or sizes at one end 28A than at another end 28B such that the fibers 28 as a group have a first diameter at one surface and a second diameter at a second surface. In such embodiments, the image size viewed or reaching one surface may be different than that of the other surface. The differing sizes or diameters at the ends of the fibers 28 may provide for example magnification, reduction or other scale changing capabilities and may be used for example if a sample 31 to be viewed is of a significantly different size than that of sensor elements 24 or if there is a need to magnify, reduce or otherwise alter scale of an image to be captured by sensor elements 24.

In FIG. 3A, a tapered fiber plate cover 26A may be mounted with the larger diameter surface on detector 22, to provide for example magnification of the sample 31. In FIG. 3B, a tapered fiber plate cover 26B may be mounted with the smaller diameter surface on detector 22 resulting in a "zooming" or reduction in the size of an image transferred onto detector 22 or sensor element 24. Other arrangements by which images may be magnified, reduced or altered as such images are transferred from an outer surface 30 to an inner surface 32 are possible.

Figure 4:
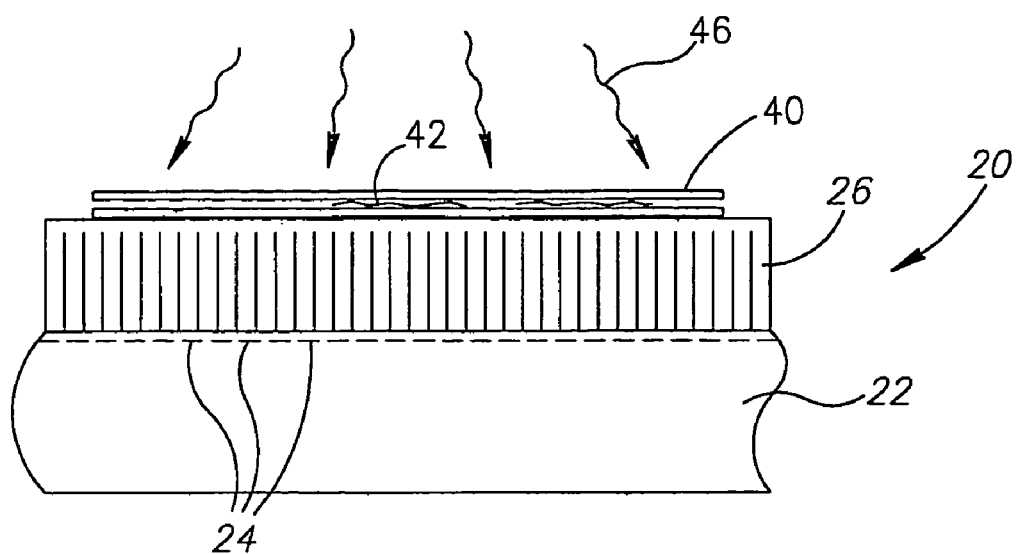
FIG. 4 is a schematic illustration of an imager suitable for viewing samples held between slides, according to an embodiment of the invention.

Reference is made to FIG. 4, a schematic illustration of an imager suitable for viewing samples held in slides, according to an embodiment of the invention. In an embodiment of the invention, glass or otherwise transparent slides such as for example a pair of microscope slides 40 may be prepared, with a sample 42 to be viewed between two glass slides 40, in a manner that may hold a sample 42 above fiber plate cover 26, similar to a process of preparing a sample 42 for viewing under a microscope. Slide 40 may be placed onto fiber plate cover 26, light 46 may be shone above slide 40 and imager 20 may be activated. Slide 40 may be removable so that other samples 42 may be imaged by imager 20.

In some embodiments, imager 20 may view sample 42 without magnification because imager 20 may image sample 42 with greater detail than can the human eye. For example, an imager having 1000×1000 sensor elements 24 of 5×5 microns may view sample 42 at an equivalent magnification of 20, assuming that the unaided human eye can view objects with a resolution of 0.1 mm. Thus, imager 20 may in some embodiments require no lens to view sample 42. Other magnification factors and other dimensions are possible, and in some embodiments a magnifying or reduction lens or other device may be used in conjunction with fiber plate cover 26.

In an alternative embodiment, a slide which may for example come in contact with fiber plate cover 26 may be replaced with a fiber plate slide, which may be made of or include a slice of fiber plate which is generally, though not necessarily, thinner than fiber plate cover 26. In such embodiment, a slide made of or including a fiber plate may take the place of glass slide 40 and may be removable from imager 20.

Figure 5A:
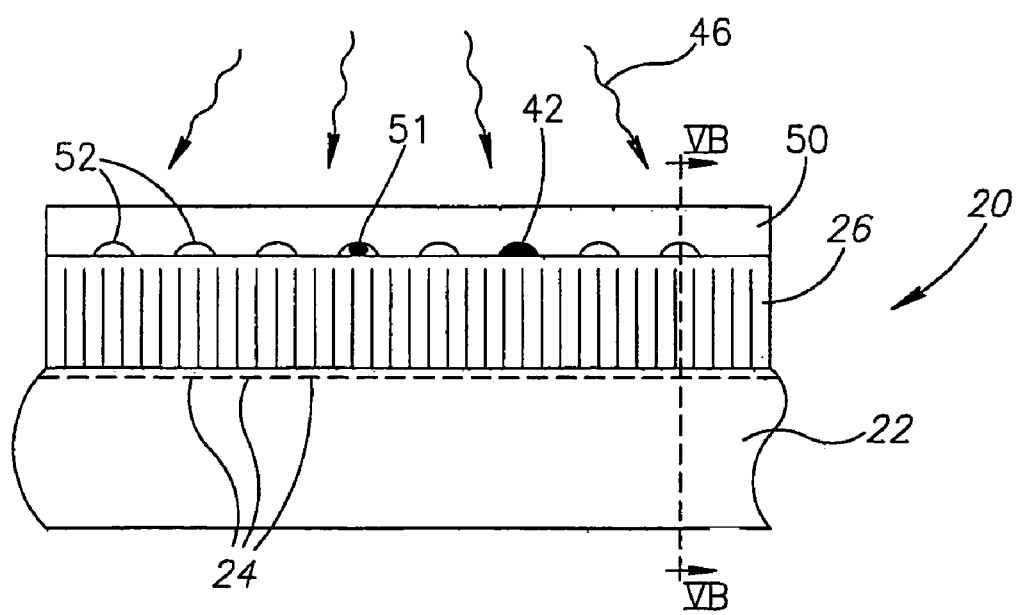
FIG. 5A is a schematic illustration of interaction chambers and an imager, in accordance with an embodiment of the invention.
Figure 5B:
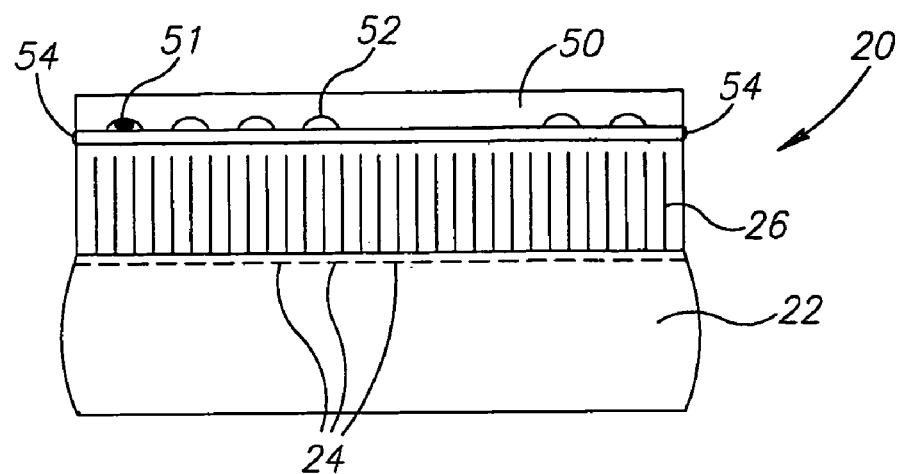
FIG. 5B is a sectional view of the application of FIG. 5A in accordance with an embodiment of the invention.

Reference is made to FIG. 5A, a schematic illustration of interaction chambers and an imager, in accordance with an embodiment of the invention. FIG. 5B is a sectional illustration of a view of FIG. 5A along the line VB-VB. In FIG. 5A, a sampling chamber 50, may be mounted or placed onto fiber plate cover 26. Sampling chamber 50 may be, for example, similar to that described in PCT Publication WO 02/055984, entitled "A System And Method For Determining In Vivo Body Lumen Conditions" which is assigned to the common assignee of the present invention and incorporated herein by reference. Other suitable sampling chambers may be used. Sampling chamber 50 may have one or a multiplicity of interaction chambers 52 into which material to be tested may be placed or sampled from an endo-luminal or other environment. In an embodiment depicted in FIG. 5A, the interaction chambers 52 may be channels etched into for example a sampling chamber 50. In some embodiments, interaction chambers 52 may be formed when sampling chamber 50 is mounted onto fiber plate cover 26. Indentations for interaction chambers 52 may in some embodiments be etched into a base material or into grooves in fiber plate cover 26. Other suitable shapes and forms for sampling chamber may be used. In one embodiment, fiber plate cover 26 is integral with sampling or interaction chambers.

In an embodiment, sample 42 may be placed or allowed to flow or collected into at least one of interaction chambers 52 and then imaged by imager 20. In another embodiment, an indicator 51 or multiple indicators 51 may be placed into interaction chambers 52 prior to placing the samples 42 therein such that reactions between the indicators 51 and the samples 42, or substances possibly contained in the sample 42, may occur in the interaction chambers 52. Indicators 51 may include for example reactants, antigens or other physical or chemical substances whose response to samples 42 may be detected, measured, imaged or otherwise recorded by imager 20 or sensor elements 24. Imager 20 may view or capture images of the results of the reactions between indicator 51 and a sample 42. If the reactions produce for example color, electromagnetic waves, heat or other reactions that may be detected by sensor elements 24, such reactions may be detected and images thereof captured by imager 20 that may detect or capture images of the colors or other responses produced by such reactions.

In some embodiments of the invention, imager 20 may be configured with for example an interaction chamber 50 attached to it. Interaction chamber 50 may contain indicators 51 such as a substance that changes color or otherwise reacts when exposed to a substance or condition that may be found in for example a body lumen, such as for example blood, particular pH, heat or other conditions that may for example be present in an in-vivo environment. In some embodiments, imager 20 may be inserted into an in-vivo environment such as for example a blood vessel or the gastro-intestinal (GI) tract. Fluids from the body lumen may flow into or through interaction chambers 52 and may be viewed by imager 20. In some embodiments, interaction chambers 52 may include a selectively permeable membrane 54 that may enable the entrance of body lumen fluids but may restrict leakage of the indicators 51 from interaction chamber 52. Such membrane 54 may retain fluids or samples 42 in an interaction chamber to facilitate a reaction between an indicator 51 in such interaction chamber 52 and a fluid or sample 42. In some embodiments, an indicator 51 may be impregnated or included in a solid that may dissolve or melt upon contact with a sample 42 in a time frame sufficient to allow imager 20 to capture an image of the reaction. In some embodiments an interaction chamber 52 may include a sponge or other absorbent material that may be impregnated with an indicator 51. In a further embodiment, a vacuum, capillary pump or other device capable of drawing or holding a sample 42 such as for example a fluid in an interaction chamber 52 may be used. In some embodiments, a membrane 54 may not be needed.

Figure 6:
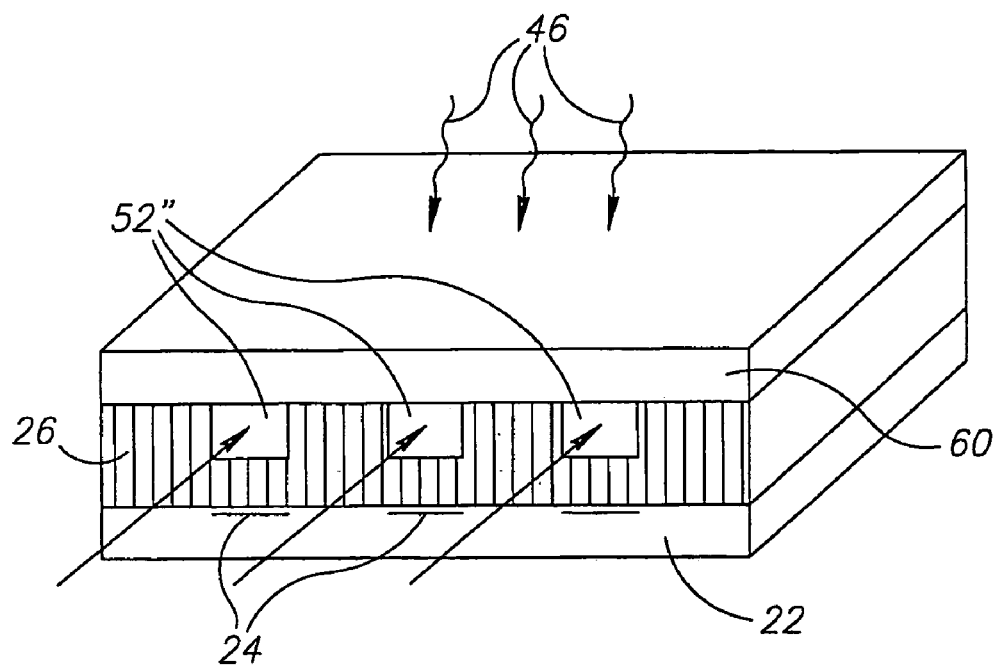
FIG. 6 is a schematic illustration of an imager and interaction chambers formed as channels, in accordance with an embodiment of the invention.

Reference is now made to FIG. 6, a schematic illustration of an imager and interaction chambers formed as channels, in accordance with an embodiment of the invention. As depicted in FIG. 6, interaction chambers 52" may be formed as channels, such as by etching or by micromachining. In some embodiments, a glass cover 60 may cover fiber plate cover 26 and may provide a further side to interaction chambers 52". FIG. 6 shows sensor elements 24 aligned with interaction chamber 52", in other embodiments, more than one sensor element 24 may be aligned to capture images of an interaction chamber 52".

Figure 7A:
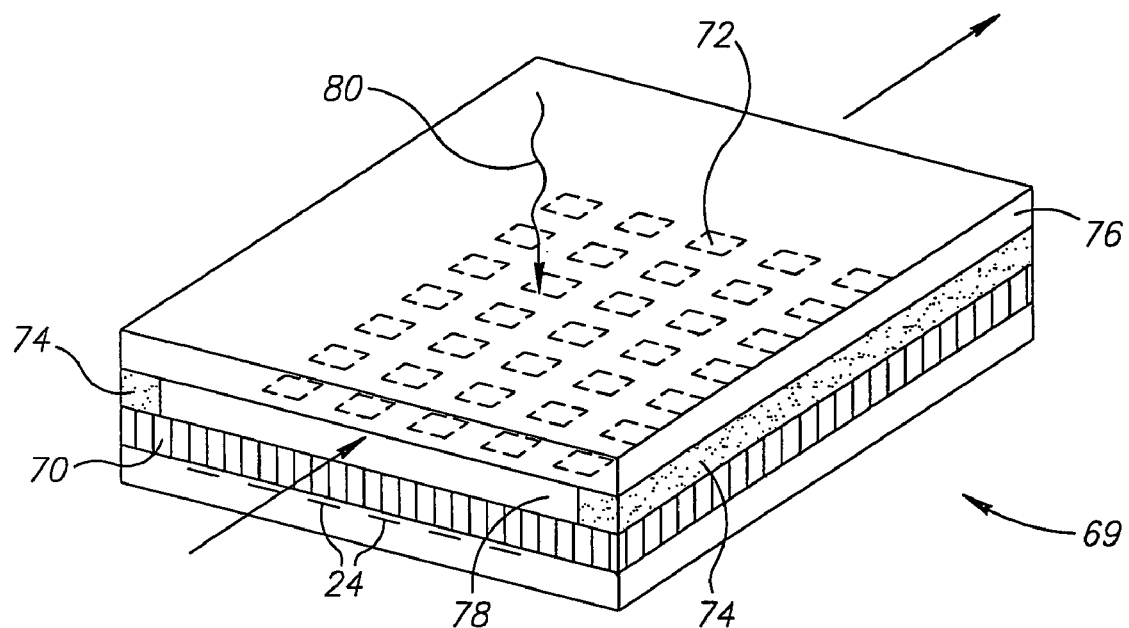
FIGS. 7A and 7B are schematic illustrations of an imager and a microarray, in accordance with an embodiment of the invention.
Figure 7B:
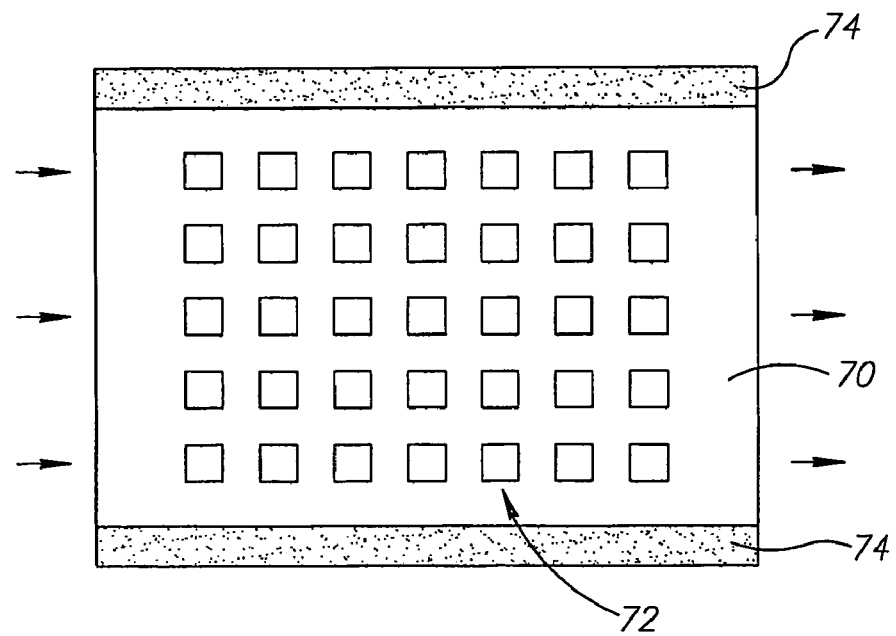

Reference is made to FIGS. 7A and 7B, schematic illustrations of an imager and a microarray or microarray analysis device, in accordance with an embodiment of the invention. As depicted in FIG. 7A, in an embodiment of the invention, imager 69 may comprise a fiber plate cover, here labeled 70, having a multiplicity of small indentations 72 therein, channel walls 74 and a cover 76 enclosing a wide channel 78 formed by for example fiber plate cover 70, channel walls 74 and cover 76. Other constructions or configuration of a microarray analysis device may be used in accordance with an embodiment of the invention. In some embodiments, indentations 72 may be etched into cover 76 or other layers of imager 69. Indentations 72 may be created, by for example etching or micromachining in fiber plate cover 70 and may be configured to hold one or more indicators. Channel 78 may be wide enough to enable fluid to flow into some or all of indentations 72 and thus enable indicators 51 to react with the fluid.

Cover 76 may be formed of for example glass or other suitable material which may be transparent to illumination 80. Upon illumination of the imager 69, sensor elements 24 may sense or capture images of reactions, changes or other elements or samples 42 in channel 78.

Reference is made to FIG. 8, a schematic flow chart diagram presentation of a method in accordance with certain embodiments of the present invention. In block 800, an imager may capture an image of a sample in contact with a fiber plate cover on such imager. Such contact may be facilitated by for example introducing a device that includes an imager into for example a body lumen where fluids or other samples in such body lumen may flow around or settle on such fiber plate cover. In other embodiments, samples may be brought into contact with a fiber plate cover by inserting samples into for example an interaction chamber or into channels of a microarray sensor such that samples may flow into the several chambers of such microarray sensor.

In some embodiments, light reaching an outer surface of the fiber plate cover may be transferred as an image of a sample through the fiber plate cover to a sensor element of an imager. In some embodiments of a method of the invention, samples may be held or enclosed in an interaction chamber where a fiber plate cover may make up for example one side of such interaction chamber or where such fiber plate cover may be otherwise attached to or contiguous to the interaction chamber.

In an embodiment of the invention, light may be transferred coherently from an outside surface of a fiber plate cover to an inside surface and on to a sensor element of the imager to which such insider surface may be attached. The size or scale of the image of a sample as it reaches the outside surface may in some embodiments be the same as the size of the sample in the image that reaches a sensor element of an imager. In some embodiments, fibers or other components of a fiber plate cover may magnify or reduce the size of the sample in the image that reaches a sensor element. In some embodiments, one or more fibers of fiber plate cover may be in contact or may transmit an image to a designated or known sensor element such that an image captured by such sensor element may be attributable to a particular sample or area of a sample in contact with the fiber plate cover. Other steps or series of steps may be used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An autonomous in vivo device comprising:
an imager; and
a fiber plate cover disposed on sensor elements of said imager, said fiber plate cover to transfer to said sensor elements an image of an object in contact with said fiber plate cover while said in vivo device passes through a body lumen, said fiber plate cover configured to be contiguous with an outer wall surrounding said in vivo device.

2. The device as in claim 1, wherein said fiber plate is configured to coherently transfer said image onto said set of sensor elements.

3. The device as in claim 1, wherein said fiber plate cover is to magnify the image transferred by said fiber plate cover.

4. The device as in claim 1, comprising an interaction chamber.

5. The device as in claim 4, comprising an indicator disposed in said interaction chamber, said indicator capable of reacting with a sample.

6. The device as in claim 5, wherein said imager is to detect a color produced by said reaction.

7. The device as in claim 1, comprising a battery.

8. The device as in claim 1, wherein said fiber plate cover is comprised of optical fibers aligned in parallel.

9. The device as in claim 1, wherein said fiber plate cover is to coherently transfer light onto said sensing element.

* * * * *